United States Patent [19]

Brahmbhatt

[11] Patent Number: 4,954,315

[45] Date of Patent: Sep. 4, 1990

[54] METHOD FOR RECOVERY OF STERILIZING GAS

[75] Inventor: Sudhir R. Brahmbhatt, Macungie, Pa.

[73] Assignee: MG Industries, Valley Forge, Pa.

[21] Appl. No.: 151,878

[22] Filed: Feb. 3, 1988

[51] Int. Cl.$^5$ .............................. A61L 2/00; F25J 3/00
[52] U.S. Cl. ......................................... 422/31; 62/11;
62/32; 62/36; 62/42; 422/34; 422/260;
422/289; 436/1
[58] Field of Search ..................... 422/31, 34, 234, 260,
422/83, 89, 115, 298, 62; 55/18; 436/1; 62/54,
11, 32, 36, 42; 549/541; 570/177–178

[56] References Cited

U.S. PATENT DOCUMENTS

| | | | |
|---|---|---|---|
| 2,488,813 | 11/1949 | Garretson | 62/54 |
| 3,341,280 | 9/1967 | Eolkin | 422/31 |
| 3,372,980 | 3/1968 | Satas | 422/34 X |
| 3,418,338 | 12/1968 | Gilman et al. | 549/541 |
| 3,420,068 | 1/1969 | Petit | 62/54 |
| 3,549,312 | 12/1970 | Ernst | 422/34 X |
| 3,644,432 | 2/1972 | Hoch et al. | 549/541 |
| 3,989,461 | 11/1976 | Skocypek et al. | 422/34 X |
| 4,010,779 | 3/1977 | Pollock et al. | 62/54 X |
| 4,047,904 | 9/1977 | Worrall | 55/18 |
| 4,077,789 | 3/1978 | Edwards | 62/54 |
| 4,122,684 | 10/1978 | Clarkson et al. | 62/54 |
| 4,249,917 | 2/1981 | Tarancon | 55/48 |
| 4,435,194 | 3/1984 | Picard et al. | 422/34 X |
| 4,555,251 | 11/1985 | Jonsson et al. | 422/34 X |
| 4,707,994 | 11/1987 | Shenoy et al. | 62/11 |
| 4,732,595 | 3/1988 | Yoshino | 62/11 |

FOREIGN PATENT DOCUMENTS

| | | | |
|---|---|---|---|
| 2745961 | 4/1979 | Fed. Rep. of Germany | 422/31 |
| 3410711 | 1/1985 | Fed. Rep. of Germany . | |
| 0185867 | 9/1966 | U.S.S.R. | 570/178 |

OTHER PUBLICATIONS

Catalog of Balston, Inc. (1982, 1985).

Primary Examiner—Robert J. Warden
Assistant Examiner—Amalia Santiago
Attorney, Agent, or Firm—William H. Eilberg

[57] ABSTRACT

The invention includes a method and apparatus for recovering one or more components of a sterilizing gas. Typically, the sterilizing gas is ethylene oxide, mixed with a relatively inert diluent such as a halocarbon. The sterilizing gas discharged from a sterilizing chamber is cryogenically cooled in a condenser, such that the ethylene oxide and the diluent are liquefied. The remaining gaseous impurities, such as air, are removed from the condenser, filtered, and vented to the atmosphere. The liquefied mixture of ethylene oxide and diluent is periodically drained from the condenser, and filtered to remove impurities. This liquid mixture can then be separated into its constituent components for later use. The liquid mixture can also be vaporized and combined with fresh ethylene oxide, as needed, to produce a fresh sterilizing gas mixture which is recycled to the sterilizing chamber. In the preferred embodiment, a gas chromatograph monitors the ethylene oxide content of the gas venting from the apparatus, so that the system can be programmed to prevent the undesired venting of ethylene oxide from the system. The gas chromatograph can also monitor the concentration of ethylene oxide in the gas being returned to the sterilizer, so that the composition of this recycled gas can be controlled. The invention makes the sterilizing process safer and more economical than processes of the prior art.

12 Claims, 1 Drawing Sheet

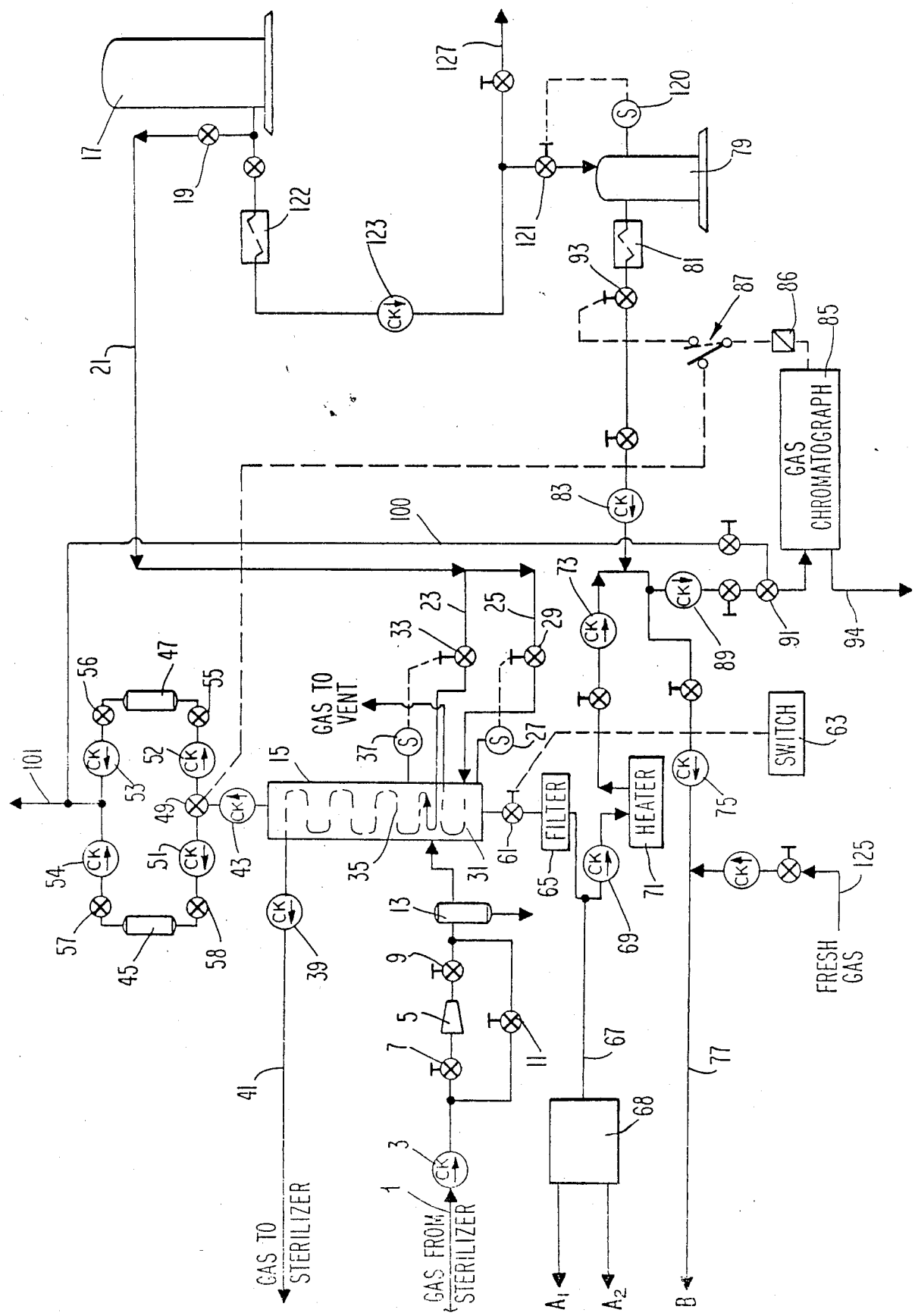

METHOD FOR RECOVERY OF STERILIZING GAS

BACKGROUND OF THE INVENTION

This invention is an apparatus and method for safe and economical treatment of a sterilizing gas. In particular, the invention provides a means for recovery of one or more components of a sterilizing gas, especially a sterilizing gas which contains ethylene oxide and a halocarbon diluent.

Ethylene oxide (ETO) is widely used as a sterilizing agent. It kills bacteria effectively after up to several hours of exposure. It is particularly useful for sterilizing articles which are sensitive to heat and moisture. Because it is highly diffusive, it can be used to sterilize multiple product combinations located within sealed plastic films, shipping cartons, and containers.

ETO is relatively expensive, so it is common to dilute the gas with a relatively inert substance such as dichlorodifluoromethane ($CCl_2F_2$), sold under the trademark Freon. It is typical to use a sterilizing gas mixture containing about 12% ETO and 88% Freon, by weight. Other diluents, such as other kinds of halocarbons, or $CO_2$, can also be used.

Unfortunately, ETO has recently been found to pose a serious health risk. It is known to be a mutagen, and is suspected of being a carcinogen. For these reasons, the federal government, and many states, have imposed requirements limiting the exposure of workers to ETO.

In the past, when the sterilizing process was completed, it was common practice to drive the sterilizing gas mixture out of the area being sterilized, and simply to vent the mixture to the atmosphere. This procedure is now clearly unacceptable, due to the known environmental hazards of ETO. Moreover, the fluorocarbons used as diluents in the sterilizing gas are now believed to harm the ozone layer of the atmosphere, and it is believed that future governmental regulations will severely limit the amount of such substances which may be discharged to the atmosphere.

In addition to being environmentally harmful, venting of both ETO and Freon is economically wasteful, since both substances are relatively expensive. The present invention makes it feasible to reclaim both components, and to re-use one or both, thereby saving money while minimizing harmful exposure.

One example of a system for reclaiming a sterilizing gas is given in U.S. Pat. No. 4,249,917. The latter patent shows a sterilization gas separation process, in which the separation of ETO is done chemically, by contacting the sterilizing gas mixture with an organic liquid solvent which absorbs the ETO. A disadvantage of the latter process is the need to provide a packed column, and a need to provide the solvent which absorbs the ETO. Both of these elements make the process more expensive. Moreover, the solvent which absorbs the ETO forms glycol, which is itself a hazardous substance, and which may be disposed of only according to approved methods, and at additional cost.

The present invention discloses a method and system which is much more economical and practical than the systems of the prior art. By recycling the ETO, the total cost ETO needed for sterilization is greatly reduced. The system of the present invention also minimizes the discharge of hazardous substances, such as ETO and Freon, into the atmosphere.

SUMMARY OF THE INVENTION

According to the present invention, sterilizing gas is discharged from a sterilizing chamber. The discharged sterilizing gas includes ETO and Freon, plus other impurities, such as air and some polymerized ETO. The discharged gas is directed into a cryogenic condenser. A cryogenic liquid, such as liquid nitrogen, cools the condenser, and liquefies the ETO and Freon. The liquid mixture is removed from the condenser and filtered to reduce or eliminate the polymerized ETO. At the same time, the gaseous impurities in the sterilizing gas, which are not liquefied, are directed out of the condenser, passed through an appropriate filter, and vented to the atmosphere.

In a first alternative, the sterilizing gas is recycled to the sterilizing chamber. In this alternative, the liquid mixture of ETO and Freon is vaporized, and a sample of the vapor is analyzed by a gas chromatograph. Additional ETO is added, as needed, to maintain the desired concentration of ETO in the mixture. Additional amounts of an ETO Freon mixture may also be added to replace the Freon lost to leakage. The recovered mixture is then directed into the sterilizing chamber.

In a second alternative, the liquid mixture of ETO and Freon is conveyed to a distillation column, where the ETO and Freon are separated. In this way, the invention enables the recovery of one or more components of the sterilizing gas, even where those components may not be immediately re-used.

Either or both of the above-described alternatives may be used, according to the invention.

With either of the above alternatives, the gas chromatograph can also be used to measure the amount of residual gaseous ETO in the mixture being vented to the atmosphere. When this amount becomes too great, the chromatograph provides a signal which causes the venting gas to be passed through a different, clean filter. The invention therefore minimizes the amount of ETO allowed to vent to the atmosphere. The same filter will also trap residual Freon in the venting gas.

It is therefore an object of the invention to provide a method and apparatus for treating a sterilizing gas.

It is another object to provide a method and apparatus for recovering one or more components of a sterilizing gas.

It is another object to provide a method and apparatus for re-using one or more components of a sterilizing gas.

It is another object to provide a method and apparatus as described above, wherein the apparatus removes various impurities from the sterilizing gas.

It is another object to reduce the amount of ethylene oxide which is allowed to escape into the atmosphere, and to minimize the hazard due to the use of ethylene oxide in a sterilizing gas.

It is another object to reduce the amount of fluorocarbons, such as Freon, which are allowed to escape into the atmosphere.

It is another object to reduce the amounts of ethylene oxide and Freon needed in a sterilization system.

It is another object to improve the cost efficiency and safety of sterilizing articles with ethylene oxide.

Other objects and advantages of the invention will be apparent to those skilled in the art, from a reading of the following brief description of the drawing, the detailed description of the invention, and the appended claims.

BRIEF DESCRIPTION OF THE DRAWING

The FIGURE is a schematic diagram of the apparatus for recovering and re-using a sterilizing gas, according to the present invention.

DETAILED DESCRIPTION OF THE INVENTION

As shown in the FIGURE, gas which has been used to sterilize objects in a sterilizing chamber (not shown) enters the system of the present invention through conduit 1, passing through check valve 3. The sterilizing gas flowing through conduit 1 (also called the "discharged sterilizing gas") contains, in general, ethylene oxide (ETO), Freon, and other impurities, including polymerized ETO, and air. The sterilizing gas in line 1 typically has a pressure of about 10–15 psig and a temperature of about 130° F. However, if the pressure of the sterilizing gas, in the sterilizing chamber, is closer to zero psig, then it is necessary to increase its pressure so that the gas will be adequately forced through the system. The pressure for this purpose can be obtained through the use of compressor 5. Moreover, if one wants to provide a mixture of liquefied ETO and Freon, suitable for delivery into a high-pressure cylinder, one needs to compress the gas even more.

If the pressure in the system is close to atmospheric pressure, then it is generally necessary to discharge the sterilizing gas by forcing another gas, such as nitrogen, at a higher pressure, into the sterilizer, to drive out the sterilizing gas.

The compressor is thus optional; if the pressure in the sterilizing chamber is greater than the operating pressure of the system, then the the compressor can be omitted. Valves 7 and 9 facilitate the removal and replacement of the compressor from the system, and valve 11 provides a bypass path for the discharged sterilizing gas, if the compressor is not present in the system, or if it is present but not being used.

The discharged gas may be passed through dryer 13, which may be a condenser that removes residual water from the gas. The dryer is also optional.

The discharged gas then passes into condenser 15. The cooling medium for condenser 15 is a cryogenic liquid. The cryogenic liquid is preferably liquid nitrogen, but other cryogenic liquids could be used. Liquid nitrogen from storage tank 17 passes through valve 19, and through conduit 21. The liquid nitrogen is split into two streams, one traveling into conduit 23 and the other entering conduit 25.

Sensor 27 is connected to measure the temperature of the contents of the bottom region of condenser 15. As indicated by the dashed line, sensor 27 is connected to operate valve 29. When the system is operating normally, the bottom region of the condenser will contain a liquid mixture of ETO and Freon. The purpose of sensor 27 and valve 29 is to insure that the ETO at the bottom of the condenser remains a liquid. Thus, if the sensor determines that the temperature of this liquid mixture is too great, the sensor causes valve 29 to open, admitting more liquid nitrogen. When the temperature is at the desired level, the sensor causes the valve to close. Liquid nitrogen passes through conduit 31, vaporizes due to the heat it absorbs, and vents to the outside, as shown. The nitrogen stream passing through conduits 25 and 31 does not contact the contents of the condenser.

The liquid nitrogen from tank 17 also enters conduit 23, and passes, through valve 33, to conduit 35, which preferably extends through all but the bottom region of condenser 15. The nitrogen in conduit 35 is responsible for lowering the temperature of the discharged sterilizing gas, so as to liquefy the ETO and Freon, and separate these components from the impurities in the sterilizing gas. Thus, the nitrogen in conduit 35 is needed only when the sterilizing chamber is being discharged, and gas is passing through the condenser. By contrast, the nitrogen in conduit 31 is needed all the time (or, at least, for a much longer fraction of the total time), because it is important that the substances at the bottom of the condenser remain liquid. Sensor 37 monitors the temperature in the middle and/or upper region of condenser 15, and operates valve 33 to allow more nitrogen into conduit 35, as needed. Conduit 35 is shown schematically as having a serpentine form; it is intended that the conduit pass through much of the indicated area of the condenser. The nitrogen in conduit 35 passes through check valve 39, and into conduit 41, where it is made available for use in the sterilizer. This nitrogen, having absorbed heat in the condenser, is vaporized, and can then be used to purge the sterilizing chamber of the sterilizing gas.

When the discharged sterilizing gas is cooled in the condenser, the ETO and Freon are liquefied, and the other gaseous components, such as air, leave the condenser through check valve 43. The exiting gas is directed through either one of filters 45 or 47, depending on the setting of three-way valve 49. The operation of the three-way valve will be described later. Check valves 51, 52, 53, and 54 assure the proper direction of flow, and valves 55, 56, 57, and 58 facilitate the removal and replacement of the filters 45 and 47 from the system.

Filters 45 and 47 are preferably filter cartridges which are commercially available. The cartridges should be of sufficient size and capacity so that each one is capable of handling all of the vented gas from the condenser. The filters remove residual ETO from the venting gas.

After passing through one of filters 45 or 47, the gas is vented to the atmosphere. Due to the separation of the ETO and Freon, from the discharged sterilizing gas, in the condenser, and due to the further action of the filter, the gas vented to the outside is virtually free of ETO and Freon.

Periodically, it is desired to remove the liquefied ETO and Freon from the bottom of condenser 15, and to use these components again in the sterilizing process. Valve 61 is operated by switch 63, to allow the liquid mixture to flow, by gravity, out of the condenser. Alternatively, if the system is operated at a higher pressure, the filter need not be located below the condenser, and the liquid may be removed by pressure, not by gravity. The liquid passes through filter 65, to remove polymerized ETO from the liquid stream. Filter 65 can be a commercially available filter, such as that which is available from Balston Incorporated, of Lexington, Massachusetts. These filters are generally made of stainless steel, and are intended for filtering liquid ETO. The liquid mixture of ETO and Freon need not be quite as cold as the liquid nitrogen cooling it, but it could be as cold as about −200° F.

The liquid leaving filter 65 may be passed through conduit 67, and directed to packed column 68, in which the ETO and Freon are separated. The ETO and Freon are then delivered through lines A₁ and A₂

The stream of liquid passing through filter 65 can also flow through check valve 69 and into heater 71. Heater 71 is preferably, but not necessarily, an electric heater, and serves to vaporize the liquid. This vaporized liquid passes through check valves 73 and 75, and into conduit 77, which leads back to the sterilizer. However, the gas leaving the heater will not, in general, have the desired proportions of ETO and Freon (preferably 12% ETO and 88% Freon). Some ETO is usually lost, due to polymerization, and due to absorption of the ETO by the product that has been sterilized. To a lesser extent, there may be a loss of Freon, due to leakage. It is therefore necessary to adjust the proportions, by adding a suitable amount of ETO, and, occasionally, by adding a fresh mixture of ETO and Freon.

Additional liquid ETO is stored in tank 79. The pressure in tank 79 is monitored by sensor 120, which controls valve 121. Liquid nitrogen from tank 17 is vaporized in vaporizer 122, flows through check valve 123, through valve 121, and into tank 79. Enough nitrogen is directed into tank 79 to maintain the pressure in the tank. Because the nitrogen is essentially inert, and virtually insoluble in the liquid ETO, little or no nitrogen will enter the system. However, to the extent that small amounts of nitrogen do enter the system, there will be no adverse effect, because of the inertness of the nitrogen.

If the system is being operated at a relatively low pressure, such as 10–15 psig, and the liquid ETO in tank 79 is stored at, say 60 psig, then the liquid will undergo a pressure drop when it passes through valve 93. This pressure drop will cause the liquid to vaporize. However, if the system is being operated at a higher pressure, say, 40–50 psig, then the pressure difference between the tank and the system is not large, and the pressure drop may not be enough to induce vaporization. In the latter case, vaporizer 81 is used. Thus, vaporizer 81 is optional; it is used only if the pressure drop is not enough to vaporize the ETO. Whether or not the vaporizer is present, the ETO passes through check valve 83, and into the line which eventually leads into conduit 77.

The flow of gaseous ETO is governed by gas chromatograph 85. The chromatograph is connected to sample the gas in the output stream, i.e. the gas flowing through check valve 73 and conduit 77. The sampled gas passes through check valve 89, through three-way valve 91, and into the chromatograph. The sample is then vented from the chromatograph through line 94.

The chromatograph is connected to switch means 87, symbolically illustrated as a single-pole double-throw switch. When switch means 87 is in the position indicated by the dotted line, chromatograph 85 is connected to flow controller 93, which is a valve that allows controllably variable amounts of ETO gas to pass through. The reading of the chromatograph, which depends on the amount of ETO in the sample stream, thus governs the amount of ETO which is added to the output stream. When the ETO content of the output stream is too low, controller 93 opens, allowing more ETO to enter the stream. Conversely, when the ETO content is too high, controller 93 closes.

The output of the chromatograph may be connected to converter 86, which could convert the chromatograph output from an electric signal to a pneumatic signal, if controller 93 is pneumatically operated. Or, if controller 93 is electrically operated, converter 86 could be a transformer, or a signal conditioner, to convert the chromatograph output to a more usable form. Converter 86 could be omitted in cases where there is no need to transform or otherwise process the signal from the chromatograph.

The gas chromatograph is also connectable, by conduit 100, to output conduit 101, through which gas vents from the system. This venting gas enters the chromatograph through three-way valve 91. Three-way valve 91 is constructed such that it allows either the gas flowing from check valve 89, or the gas flowing through conduit 100, to enter the chromatograph, but not both at once. When three-way valve 91 is set so that the gas in conduit 100 can enter the chromatograph, switch 87 must also be set to the position indicated by the solid line. That is, when the chromatograph is sampling gas from the conduit 100, it is also operatively connected to three-way valve 49. When the amount of ETO in conduit 100 is too great, it means that the filter (either 45 or 47, whichever is currently being used) needs to be replaced. The chromatograph then generates a signal causing three-way valve 49 to change position, i.e. to divert the output stream from the condenser into the filter which was not being used. Thus, if the filter currently used is filter 45, and the concentration of ETO in the venting conduit becomes too great, the valve will divert the stream to filter 47. If the filter currently used is filter 47, the valve will divert the stream to filter 45. The filter which was previously used can then be replaced, while the system continues to operate with the other filter.

The gas chromatograph is periodically switched, by switch means 87, so that it can perform both of its two functions. These functions include analyzing the output stream of sterilizing gas, which is about to be fed back to the sterilizer, and monitoring the gas being discharged into the atmosphere to be sure that the proportion of ETO is within desired limits. The chromatograph can perform only one of these functions at one time. It is also possible, though more costly, to provide two chromatographs, both operating continuously, and dedicated to the separate functions described above.

Under normal operation, each sterilizing cycle depletes some of the ETO, due to formation of ETO polymers, and due to absorption of ETO by the product being sterilized. The polymers are removed by filter 65, and are lost to the system. The Freon is depleted at a much slower rate, due to leakage. The depleted ETO is replenished from tank 79, as discussed above. To replace the Freon which may be lost to leakage, after repeated operation, one can inject a fresh mixture of gaseous ETO and Freon into conduit 77, as indicated at conduit 125. The ETO in conduit 125 can be derived from tank 79, or it can come from a separate supply.

Conduit 127 provides an alternative source of nitrogen gas which can be used to purge the sterilizing chamber. The nitrogen in conduit 127, having been vaporized in vaporizer 122, is relatively warm, and may even be at room temperature. In some applications, it is preferred that the nitrogen gas used to purge the chamber be at room temperature. By contrast, the nitrogen gas in conduit 41, having been first vaporized upon passing through the condenser, is still quite cold.

The present invention therefore yields two different kinds of products. First, it is capable of recovering the individual components of the sterilizing gas, i.e. ETO and Freon, and storing these components separately for later use in a sterilizing process, or for other purposes. Secondly, it is capable of purifying and recycling the sterilizing gas, with the addition of more ETO, as needed. The invention can be operated to perform either or both of these functions. In other words, the apparatus associated with conduit 67 and the apparatus associated with conduit 77 can both be considered to be optional. Whichever alternative is used, the amounts of ETO and Freon vented to the atmosphere are minimized, and the total amounts consumed are reduced.

Although the invention has been described with respect to a specific embodiment, it is understood that the invention can be modified. As stated above, many of the individual components are optional, and need be used only in certain applications. The particular materials used for the filters, the medium used to cool the sterilizing gas, and the means of supplying additional ETO can all be modified. The invention is also not limited to the use of ETO as a sterilizing agent or to Freon as a diluent. Other agents and diluents can be used, within the scope of the invention. These and other similar modifications should be deemed within the spirit and scope of the following claims.

What is claimed is:

1. A method for recovery of a sterilizing gas, the sterilizing gas including a sterilizing agent and a relatively inert diluent, the sterilizing gas having been discharged from a sterilizing chamber, the method comprising the steps of:
   (a) directing a sterilizing gas into a condenser, the condenser including an upper section and a lower section,
   (b) cooling the upper section of the condenser to a temperature sufficient to liquefy the sterilizing agent and a diluent gas, so as to produce a liquid mixture of the sterilizing agent and the diluent, but not sufficient to liquefy other gaseous impurities mixed with the sterilizing gas,
   (c) maintaining the lower section of the condenser at a temperature sufficient to keep the liquid mixture in the liquid state, the maintaining step comprising the step of cooling said lower section, the maintaining and cooling steps being performed by separately operable cooling means,
   (d) venting the gaseous impurities remaining after the cooling steps,
   (e) vaporizing the mixture of sterilizing agent and diluent,
   (f) adjusting the proportion of sterilizing agent in the vaporized mixture by adding more sterilizing agent, the vaporizing and adjusting steps being performed outside of the condenser, and
   (g) returning the vaporized mixture to the sterilizing chamber,
wherein all steps of the method are performed repeatedly without adding additional diluent only.

2. The method of claim 1, further comprising the step of distilling at least a portion of the liquid mixture produced in step (b), so as to separate the liquefied sterilizing agent from the liquefied diluent.

3. The method of claim 1, wherein the adjusting step is preceded by the step of measuring the proportion of sterilizing agent in the vaporized mixture.

4. A method for recovery of a sterilizing gas, the sterilizing gas including a sterilizing agent and a relatively inert diluent, the sterilizing gas having been discharged from a sterilizing chamber, the method comprising the steps of:
   (a) cooling a sterilizing gas, to a temperature sufficient to liquefy a sterilizing agent and a diluent gas so as to produce a liquid mixture of the sterilizing agent and the diluent, but not sufficient to liquefy other gaseous impurities mixed with the sterilizing gas,
   (b) venting the gaseous impurities remaining after the cooling step,
   (c) vaporizing the mixture of sterilizing agent and diluent,
   (d) adjusting the proportion of sterilizing agent in the vaporized mixture by adding more sterilizing agent, and
   (e) returning the vaporized mixture to the sterilizing chamber,
wherein all steps of the method are performed repeatedly without adding additional diluent only.

5. The method of claim 4, further comprising the step of distilling at least a portion of the liquid mixture produced in step (a), so as to separate the liquefied sterilizing agent from the liquefied diluent.

6. A method for recovery of a relatively inert diluent, the diluent being one of two primary components of a sterilizing gas, the other primary component being a sterilizing agent, the sterilizing gas having been discharged from a sterilizing chamber, the method comprising the steps of:
   (a) directing a sterilizing gas into a condenser, the condenser including an upper section and a lower section,
   (b) cooling the upper section of the condenser to a temperature sufficient to liquefy a sterilizing agent and a diluent gas, so as to produce a liquid mixture of the sterilizing agent and the diluent, but not sufficient to liquefy other gaseous impurities mixed with the sterilizing gas,
   (c) cooling the lower section of the condenser at a temperature sufficient to keep the liquid mixture in the liquid state, the two cooling steps being performed by separately operable cooling means,
   (d) venting the gaseous impurities remaining after the cooling steps,
   (e) distilling at least a portion of the liquid mixture remaining in the lower section of the condenser, so as to separate the liquefied sterilizing agent from the liquefied diluent, wherein all steps of the method are repeatedly performed without adding additional diluent only.

7. A method for recovery of components of a sterilizing gas, the sterilizing gas including a sterilizing agent and a relatively inert diluent, the sterilizing gas having been discharged from a sterilizing chamber, the method comprising the steps of:
   (a) cooling a sterilizing gas to a temperature sufficient to liquefy a sterilizing agent and a diluent gas so as to produce a liquid mixture of the sterilizing agent and the diluent, but not sufficient to liquefy other gaseous impurities mixed with the sterilizing gas,
   (b) venting the gaseous impurities remaining after the cooling step,
   (c) distilling the liquid mixture so as to separate the liquefied sterilizing agent from the liquefied diluent, wherein all steps of the method are repeatedly performed without adding additional diluent only.

8. A method for recovery of a relatively inert diluent, the diluent being one of two primary components of a sterilizing gas, the other primary component being a sterilizing agent, the sterilizing gas having been discharged from a sterilizing chamber, the method comprising the steps of:
  (a) cooling a sterilizing gas to a temperature sufficient to liquefy a sterilizing agent and a diluent gas so as to produce a liquid mixture of the sterilizing agent and the diluent, but not sufficient to liquefy other gaseous impurities mixed with the sterilizing gas,
  (b) venting the gaseous impurities remaining after the cooling step,
  (c) distilling the liquid mixture so as to separate the liquefied sterilizing agent from the liquefied diluent, wherein all steps of the method are repeatedly performed without adding additional diluent only.

9. A method for recovery of a sterilizing gas, the sterilizing gas including a sterilizing agent and a relatively inert diluent, the sterilizing gas having been discharged from a sterilizing chamber, the method comprising the steps of:
  (a) directing a sterilizing gas into a condenser, the condenser including an upper section and a lower section,
  (b) cooling the upper section of the condenser to a temperature sufficient to liquefy the sterilizing agent and a diluent gas, so as to produce a liquid mixture of the sterilizing agent and the diluent, but not sufficient to liquefy other gaseous impurities mixed with the sterilizing gas,
  (c) maintaining the lower section of the condenser at a temperature sufficient to keep the liquid mixture in the liquid state, the maintaining step comprising the step of cooling said lower section, the maintaining step of (c) and cooling step of (b) being performed by separately operable cooling means,
  (d) venting the gaseous impurities remaining after the cooling steps in (b) and (c),
  (e) vaporizing the mixture of sterilizing agent and diluent,
  (f) adjusting the proportion of sterilizing agent in the vaporized mixture by adding more sterilizing agent, the vaporizing and adjusting steps being performed outside of the condenser, the adjusting step being performed without adding additional diluent only, except for the occasional addition of fresh sterilizing gas mixture to compensate for leakage, and
  (g) returning the vaporized mixture to the sterilizing chamber.

10. The method of claim 9, wherein the diluent is a fluorocarbon.

11. The method of claim 4, wherein the diluent is a fluorocarbon.

12. The method of claim 6, wherein the diluent is a fluorocarbon.

* * * * *